(12) United States Patent
Roos et al.

(10) Patent No.: US 8,360,068 B2
(45) Date of Patent: Jan. 29, 2013

(54) EAR CUP

(75) Inventors: Anders Roos, Värnamo (SE); Joakim Birgersson, Vetlanda (SE)

(73) Assignee: MSA Sordin AB, Varnamo (SE)

( * ) Notice: Subject to any disclaimer, the term of this patent is extended or adjusted under 35 U.S.C. 154(b) by 260 days.

(21) Appl. No.: 12/087,361

(22) PCT Filed: Jan. 23, 2007

(86) PCT No.: PCT/SE2007/000060
§ 371 (c)(1),
(2), (4) Date: Aug. 29, 2008

(87) PCT Pub. No.: WO2007/086793
PCT Pub. Date: Aug. 2, 2007

(65) Prior Publication Data
US 2009/0014014 A1    Jan. 15, 2009

(30) Foreign Application Priority Data
Jan. 24, 2006    (SE) ...................................... 0600145

(51) Int. Cl.
*A61F 11/00* (2006.01)
*H04R 25/00* (2006.01)
(52) U.S. Cl. .................. 128/864; 128/866; 381/372
(58) Field of Classification Search .................. 128/864, 128/866, 867; 381/372
See application file for complete search history.

(56) References Cited

U.S. PATENT DOCUMENTS 5,241,971 A * 9/1993 Lundin ......................... 128/864
6,151,717 A * 11/2000 Lindgren et al. ................ 2/209

FOREIGN PATENT DOCUMENTS

| CN | 2409941 | 12/2000 |
| GB | 258732 | 9/1926 |
| WO | WO 90/15584 | 12/1990 |
| WO | WO 9015584 A1 * | 12/1990 |

OTHER PUBLICATIONS

Chinese Office Action dated Oct. 16, 2009, issued in Chinese Application No. 200780002242.2.
Chinese Office Action dated Jul. 15, 2010, issued in Chinese Application No. 200780002242.2.

* cited by examiner

*Primary Examiner* — Patricia Bianco
*Assistant Examiner* — Victoria J Hicks
(74) *Attorney, Agent, or Firm* — Harness, Dickey & Pierce, P.L.C.

(57) ABSTRACT

Example embodiments relate to an ear cup for use in a hearing protector unit including two ear cups, and a device to fasten the hearing protector unit to a wearer's head, the device being connected to the ear cups. The ear cup may include a cup portion with a support surface; and a sealing device, placed against the support surface of the cup portion and intended to bear against a wearer's head in an area around an ear of the wearer. The sealing device may include a sealing portion of a soft material, which includes a peripherally extending circumference slot and which, in its periphery area, bears against the support surface with an opening of the circumference slot directed towards the cup portion, a sound-attenuating ring, situated in the circumference slot of the sealing portion, and a clamping ring of a rigid material, situated in the circumference slot of the sealing portion to expand the sealing portion produced from soft material, the sealing portion being provided with a peripherally extending flange, introduced in the cup portion such that it bears against an inner side of the cup portion, whereby the clamping ring bears against the flange and presses the flange against the inner side of the cup portion for fastening the sealing device to the cup portion.

8 Claims, 2 Drawing Sheets

EAR CUP

FIELD OF THE INVENTION

This application is a national stage entry of PCT/SE2007/000060 filed Jan. 23, 2007 and claims the benefit of Swedish application 0600145-7 filed Jan. 24, 2006.

The present invention relates to an ear cup, which is intended to be used in a hearing protector unit that has two ear cups and a means for fastening the hearing protector unit to a wearer's head, the means being connected to the ear cups, the ear cup having a cup portion with a support surface as well as a sealing device, placed against the support surface of the cup portion for bearing against a wearer's head in an area around an ear of the wearer.

BACKGROUND ART

In prior art ear cups of this type, the sealing device is produced from a frame of rigid plastic, a ring of foam plastic and a PVC-film. The ring is placed on the frame, the PVC-film is placed on the ring and is then welded on the frame such that an indivisible unit is formed. The frame of the sealing device is fastened onto the cup portion of the ear cup. The frame and the cup portion are both produced from rigid plastic, whereby rigid material bears against rigid material. If a surface of the frame that bears against the support surface of the cup portion has a shape that differs from the shape of the support surface, this will result in a poor sealing and, thereby, an unsatisfactory noise attenuation. A drawback with such a sealing device is thus that it may allow proportionally much noise to pass through, such that the noise attenuating effect is impaired.

SUMMARY OF THE INVENTION

The object of the invention is therefore to provide an ear cup that is designed so as to eliminate the above drawback, i.e. such that a good sealing is achieved between the cup portion and the sealing device, even if the surface of the sealing device that bears against the support surface of the cup portion has a shape that differs from the shape of the support surface.

This object is achieved according to the invention by an ear cup of the kind described above, which is characterized in that the sealing device comprises a sealing portion of a soft material, such as rubber, which has a peripherally extending circumference slot, and which in its periphery area bears against said support surface with the opening of the circumference slot directed towards the cup portion, a sound-attenuating ring, which is placed in the circumference slot of the sealing portion, and a clamping ring of a rigid material, such as rigid plastic, which is situated in the circumference slot of the sealing portion to expand the sealing portion produced from soft material, and in that the sealing portion is provided with a peripherally extending flange, which is introduced in the cup portion such that it bears against the inner side of the cup portion, whereby the clamping ring bears against the flange and presses the flange against the inner side of the cup portion for fastening the sealing device to the cup portion.

The sound-attenuating ring can be produced in one piece together with the sealing portion and from the same soft material as the sealing portion. For this embodiment, the clamping ring and the sealing portion with the sound-attenuating ring can constitute one moulded unit.

BRIEF DESCRIPTION OF THE DRAWINGS

The invention will in the following be described in more detail with reference to the accompanying drawings.

DESCRIPTION OF PREFERRED EMBODIMENTS

Figure 1:
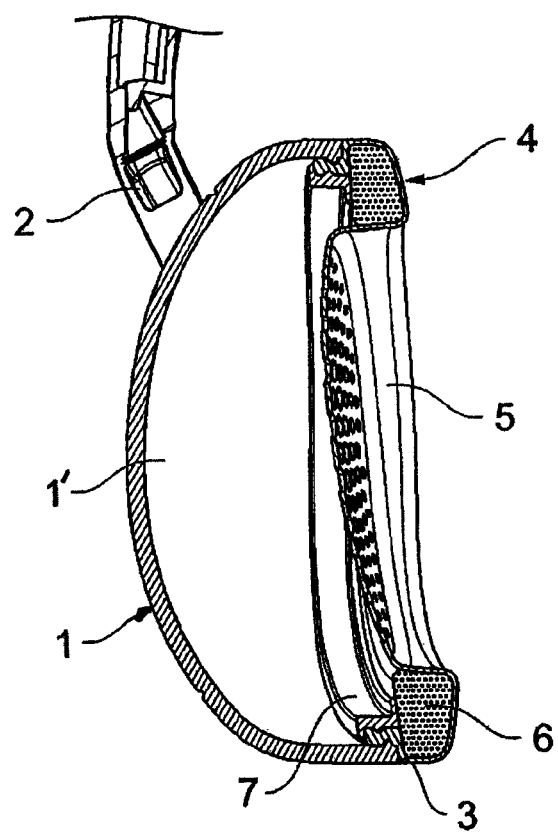
FIG. 1 is a sectional view showing an ear cup according to the invention.

A hearing protector unit has two ear cups 1, from which only one is shown in FIG. 1. The ear cups 1 are connected to each other by a headband 2 for fastening the hearing protector unit on a wearer's head. In an alternative embodiment, the two ear cups 1 can have, instead of the headband 2, a mounting each, which is adapted to be fixed to a helmet or the like, to be worn by the user. Each of the ear cups 1 has a cup portion 1', which preferably is produced from rigid plastic.

The cup portion 1' shown in FIG. 1 has a peripherally extending support surface 3, against which a sealing device 4 attached to the cup portion bears. The sealing device 4 is adapted to bear against the wearer's head in the area around one of the wearer's ears.

Figure 2:
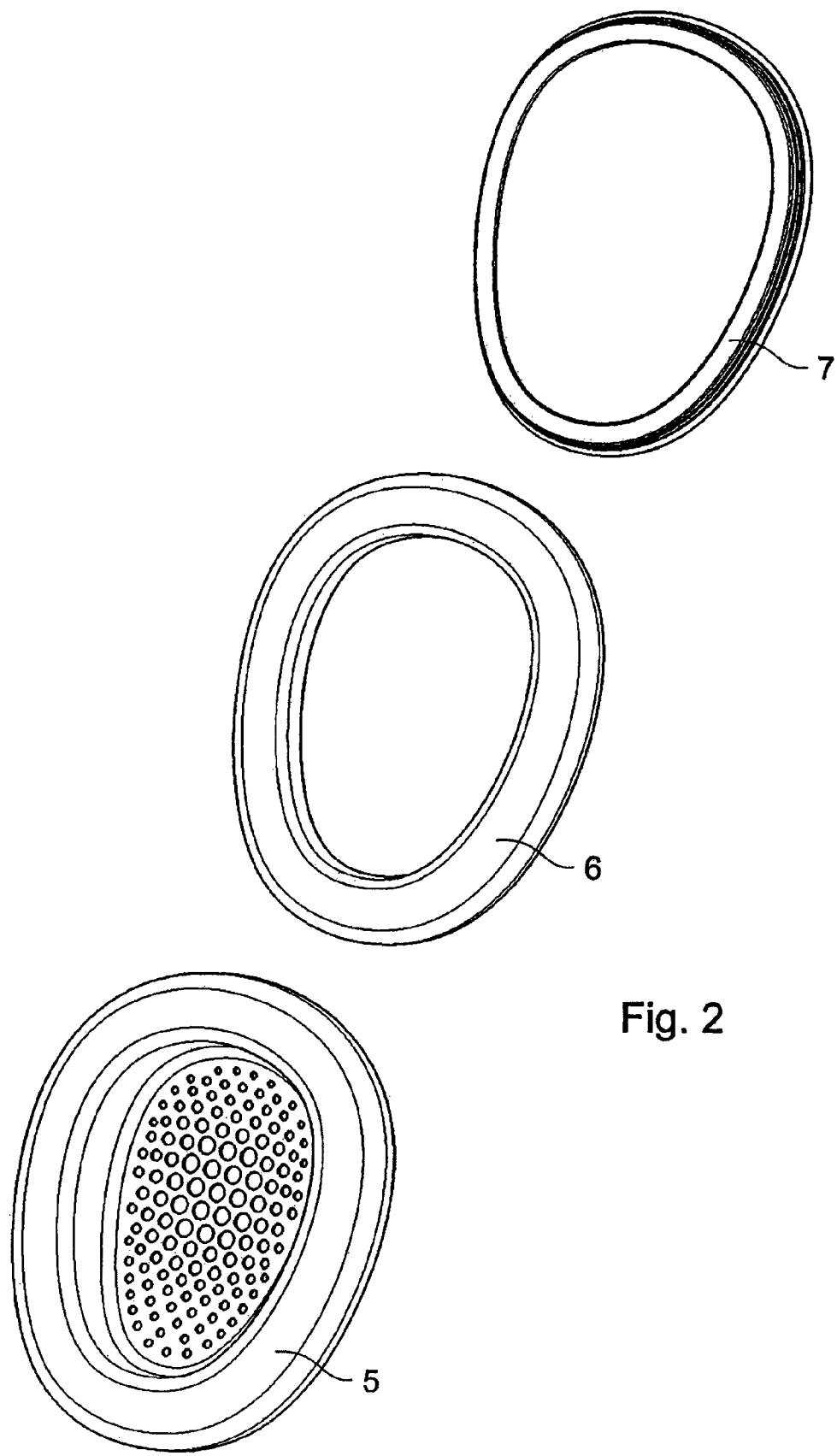
FIG. 2 is an exploded view showing parts of a sealing device of an ear cup according to the invention.

The shown sealing device 4 consists of three separate parts, namely a sealing portion 5, a sound-attenuating ring 6 and a clamping ring 7 (see FIG. 2).

Figure 3:
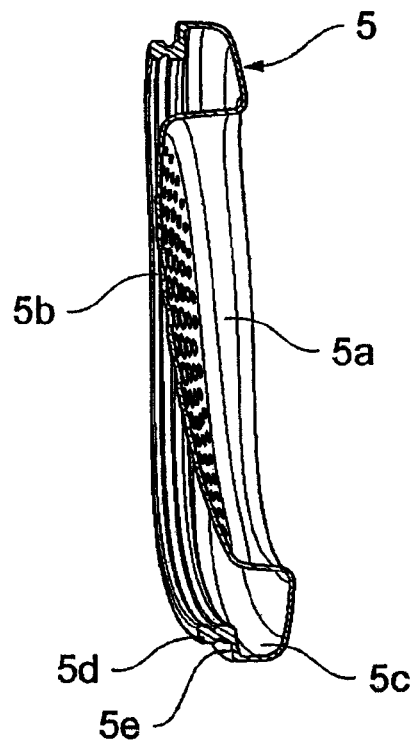
FIG. 3 is a sectional view showing a sealing portion of the sealing device.

From FIG. 3 it appears that the sealing portion 5 is cup-formed and has a cup opening 5a, a cup bottom 5b and a peripherally extending circumference slot 5c. The cup opening 5a is directed towards the wearer's ear, i.e. away from the cup portion 1', and the opening of the circumference slot 5c is directed towards the cup portion 1'. In the cup bottom 5b, holes are punched to facilitate circulation of air. The sealing portion 5 is produced from soft rubber material, such as TPE. The sealing portion 5 is further equipped with a peripherally extending flange 5d that is snapped in the cup portion 1' for fastening the sealing device 4 thereon. Outside the peripherally extending flange 5d, the sealing portion 5 has a peripherally extending bearing surface 5e, which bears against the support surface 3.

The sound-attenuating ring 6, which is produced from foam plastic, is situated in the circumference slot 5c of the sealing portion 5, and bears against the bottom of the slot 5c. The thickness of the sound-attenuating ring 6, i.e. its extension in axial direction, can be varied as required.

The clamping ring 7 is located in the circumference slot 5c of the sealing portion 5, outside the sound-attenuating ring 6. The clamping ring 7 bears against the flange 5d and expands the sealing portion 5 produced from soft rubber material in order to press the flange 5d against the inner side of the cup portion 1'. Moreover, the clamping ring 7 holds the sound-attenuating ring 6 in place in the circumference slot 5c of the sealing portion 5. The clamping ring 7 is preferably produced from rigid plastic.

In a not shown alternative embodiment, the sealing device 4 is formed as one unit, whereby the sound-attenuating ring 6 is produced in one piece with the sealing portion 5 and of the same soft rubber material as the sealing portion and the clamping ring 7 and the sealing portion 5 with the sound-attenuating ring 6 constitute one moulded unit.

The invention claimed is:

1. An ear cup for use in a hearing protector unit including two ear cups, and a device to fasten the hearing protector unit to a wearer's head, the device being connected to the ear cups, the ear cup comprising:
- a cup portion having an innermost diameter surface and an outer surface; and
- a sealing device intended to bear against a wearer's head in an area around an ear of the wearer, the sealing device including:
  - a sealing portion of a soft material, which includes a peripherally extending circumference slot and which, in its periphery area, bears against said inner diameter surface with an opening of the circumference slot directed towards the cup portion,
  - a sound-attenuating ring, situated in the circumference slot of the sealing portion, and
  - a clamping ring of a rigid material, the clamping ring having an outermost surface secured entirely along the innermost diameter surface of the cup portion situated in the circumference slot of the sealing portion to expand the sealing portion produced from soft material, the sealing portion being provided with a peripherally horizontally extending flange, introduced in the cup portion such that the clamping ring bears against the inner diameter surface of the cup portion, the inner diameter surface being a surface of the cup portion pointing towards a center of the cup portion, whereby the clamping ring bears against the flange and presses the flange against the inner diameter surface of the cup portion for fastening the sealing device to the cup portion.

2. The ear cup according to claim 1, wherein the sound-attenuating ring is produced in one piece with the sealing portion and from the same soft material as the sealing portion.

3. The ear cup according to claim 2, wherein the clamping ring, the sealing portion, and the sound-attenuating ring constitute one unit that is molded.

4. A hearing protector unit including at least one ear cup according to claim 3, and a device to fasten the hearing protector unit to a wearer's head.

5. A hearing protector unit including at least one ear cup according to claim 1, and a device to fasten the hearing protector unit to a wearer's head.

6. A hearing protector unit including at least one ear cup according to claim 2, and a device to fasten the hearing protector unit to a wearer's head.

7. The ear cup according to claim 1, wherein the sealing device includes a sealing portion of rubber.

8. The ear cup according to claim 1, wherein the clamping ring is of a rigid plastic.

* * * * *